United States Patent [19]
Srivastava et al.

[11] Patent Number: 5,525,719
[45] Date of Patent: Jun. 11, 1996

[54] N-PROTECTED-2'-O-METHYL-AND N-PROTECTED-3'-O-METHYL-RIBONUCLEOSIDES AND THEIR PHOSPHORAMIDITE DERIVATIVES

[75] Inventors: Saresh C. Srivastava; Syed K. Raza, both of Waltham, Mass.

[73] Assignee: Chemgenes Corporation, Waltham, Mass.

[21] Appl. No.: 65,016

[22] Filed: May 24, 1993

Related U.S. Application Data

[63] Continuation-in-part of Ser. No. 753,077, Aug. 30, 1991, Pat. No. 5,214,135.
[51] Int. Cl.⁶ .................... C07H 19/067; C07H 19/10; C07H 19/167; C07H 19/20
[52] U.S. Cl. .................. 536/26.7; 536/26.8; 536/27.62; 536/27.81; 536/28.51; 536/28.53; 536/25.34
[58] Field of Search ..................... 536/26.7, 26.74, 536/26.8, 27.8, 27.62, 27.81, 28.51, 28.53

[56] References Cited

U.S. PATENT DOCUMENTS 5,214,135  5/1993  Srivastava et al. ............... 536/26.7

FOREIGN PATENT DOCUMENTS

| | | | |
|---|---|---|---|
| 0260032 | 3/1988 | European Pat. Off. | 536/24.2 |
| 0339842 | 11/1989 | European Pat. Off. | 514/044 |
| 4110085 | 10/1992 | Germany | 536/24.5 |
| 2264792 | 4/1989 | Japan | 536/25.3 |

OTHER PUBLICATIONS

Hirao et al., "Synthesis and Properties of an Initiation Codon Analog Consisting of 2'-O- methyl Nucleosides," *Nucleosides Nucleotides*, 9(8), 1113–1122 (1990); *Chem. Abstr.*, 114(21), p. 873, Abstr. No. 207676t (1991).

Kierzek et al., "Some Steric Aspects of Synthesis of Oligoribonucleotides by Phosphoamidite Approach on Solid Support," *Bull. Pol. Acad. Sic., Chem.*, 35(11–12), 507–516 (1988); *Chem. Abstr.*, 110(7), p. 126, Abstr. No. 57990s (1989); only Abstract supplied.

Leonard et al., "A Convenient Preparation of Protected 2'-O-Methylguanosine," *Nucleosides Nucleotides*, 11(6), 1201–1204 (1992); *Chem. Abstr.*, 117(17), p. 895, Abstr. No. 171915r (1991); only Abstract supplied.

Yamana et al., "Synthesis and Properties of Oligonucleotides Bearing a Pendant Pyrene Group," in Thirteenth Symposium on Nucleic Acids Chemistry, *Nucleic Acids Symposium Series*, No. 16, IRL PRess, Washington, D.C., 1985, pp. 169–172.

Wagner et al., "A Simple Procedure for the Preparation of Protected 2'-O-Methyl or 2'-O-Ethyl Ribonucleoside-3'-O-phosphoramidites," *Nucleic Acids Res.*, 19(21), 5965–5971 (1991).

Venijaminova et al., "Oligo(2'-O-Methylribonucleotides)and Their Derivatives. I. Automatic H-Phosphonate Synthesis of the Oligo(2'-O-Methylribonucleotides) Via H-Phosphonates," *Bioorg. Khim.*, 16(5), 635–642 (1990); English abstract, Russian text.

Inoue et al., "Synthesis and Hybridization Studies on Two Complementary Nona(2'-O-Methyl)ribonucleotides," *Nucleic Acids Res.*, 15(15),6131–6148 (1987).

Shibahara et al., "Site–directed Cleavage of RNA," *Nucleic Acids Res.*, 15(11), 4403–4415 (1987).

Alexandrova et al., "Synthesis of Cytidylyl–(3'–5')–2'–O(and 3'–O)–Methyladenosine 3'–O(and 2'–O)–N–Formyl–L–methionyl Derivatives," *Coll. Czech. Chem. Comm.*, 42, 1694–1704 (1977).

Alexandrova et al., "Synthesis of Cytidylyl–(3'–5')–Cytidylyl–(3'–5')Adenosine Derivatives," *Coll. Czech. Chem. Comm.*, 42, 1686–1693 (1977).

Gladkaya et al., "Synthesis of N,O–Protected Derivatives of 2'–O–Methylcytidine and 2'–O–Methyl–and $N^1$ –Methylguanosines," *Khim. Prir. Soedin.*, 1989(4), 568–573; *Chem. Abstr.*, 112(21), p. 772, Abstr. No. 198947m (1990).

Ishido et al., "Process for Synthesizing Oligonucleotides in a Homogeneous System Using Polysaccharide Derivatives as High Molecular Weight Protective Groups," PCT WO 88 03,149, published 05 May 1988; *Chem. Abstr.*, 109(25), p. 910, Abstr. No. 231471q (1988); only abstract provided.

Rozners et al., "Synthesis of Oligoribonucleotides by the H–Phosphonate Method Using Base–Labile 2'–O–Protecting Groups, II. Some Aspects of Use of 2'–O–benzolyl and Anisoyl Protecting Groups," *Bioorg. Khim.*, 16(11), 1531–1536 (1990).

Cotten et al., "2'–O–Methyl, 2'–O–Ethyl Oligoribonucleotides and Phosphorothioate Oligoribonucleotides as Inhibitors of the in vitro U7 snRNP–Dependent mRNA Processing Event," *Nucleic Acids Res.*, 19(10), 2629–2635 (1991).

Borowy–Borowski, et al., "Study of side Reactions Occurring during Synthesis of Oligodeoxynucleotides Containing $O^6$ –Alkyldeoxyguanosine Residues at preselected Sites," *Biochemistry* 26:2465 (1987).

(List continued on next page.)

Primary Examiner—John Kight, III
Assistant Examiner—L. Eric Crane
Attorney, Agent, or Firm—Hale and Dorr

[57] ABSTRACT

This invention is directed to processes for producing high purity N-protected-2'-O-methyl-5'-dimethoxytrityl-3' ribonucleoside methoxy, N,N-diisopropyl phosphoramidites (group 1), and N-protected-2'-O-methyl-5'-dimethoxytrityl-3'-ribonucleoside ethoxy, N,N-diisopropyl phosphoramidites (group 2). This invention is further directed to the process for producing high purity 2'-O-methyl-5'-dimethoxytrityl-inosine (structure IX; group 3), and 2'-O-methyl-5'-dimethoxytrityl-inosine-3'-cyanoethyl, N,N-diisopropyl phosphoramidite (structure Xa; group 3). This invention is also directed to the process for producing high purity N-protected-3'-O-methyl-5'-dimethoxytrityl ribonucleosides (group 6), and N-protected-3'-O-methyl-5'-dimethoxytrityl-2'-ribonucleoside cyanoethyl, N,N-diisopropyl phosporamidites (group 7).

5 Claims, 4 Drawing Sheets

OTHER PUBLICATIONS

Fujii, et al., "Use of the (Butylthio) Carbonyl Group to Protect Uracil and Guanine Residues in Oligoribonucleotide Synthesis," *Chem. Pharm. Bull.* 35(7):3066–3069 (1987).

Gaffney, et al., "Synthesis and Characterization of a Set of Four Dodecadeoxyribonucleoside Undecaphoshates Containing $O^6$ –Methyguanine opposite Adenine, Cytosine, Guanine, and Thymine", *Biochemistry*, 23:5691–5696 (1984).

Inoue, H., et., al "Sequence–dependent hydrolysis of RNA using modified oligonucleotide splints and RNase H," *FEBS Letters 215:327–330 (1987)*.

Kamimura, et al., "Oligoribonucleotide Synthesis by Use of Nucleotide Units Masked with New Protecting Groups On The Base Residues of Guanosine and Uridine, " *Nucleic Acids Research Symposium Series*, No. 12, IRL Press Ltd., Oxford England, 1983, pp. 63–65.

Kjellberg, et al., "Studies on the Alkylation of Derivatives of Guanine," *Nucleosides & Nucleotides 8(2): 225–256 (1989)*.

Kochetkov, et al., *Organic Chemistry of Nucleic Acids*, Part B Plenum Press, New York, 1972, pp. 458–460.

Sproat, B. S., et al., "New synthetic routes to protected purine 2'–O–methylriboside–3'–O–phosphoramidites using a novel alkylation procedure," *Nucleic Acids Research* 18: 41–49 (1990).

Takaku, et al., "Use of 3,4–Dimethoxybenzyl Group As A Protecting Group For The 2'–Hydroxyl Group In The Synthesis of Oligo–Ribonucleotides," *Chemistry Letters*, 1005–1008 (1986).

Kierzek et al., "Some Steric Aspects of Synthesis of Oligoribonucleotides by Phosphoramidite Approach on Solid Support," *Bull. Pol. Acad. Sci., Chem.*, 35(11–12), 507–516 (1988); complete copy of original publication.

Caruthers et al., "Synthesis of Oligonucleotides Using the Phosphoramidite Method," in *Biophosphates and Their Analogues–Synthesis, Structure, Metabolism and Activity*, report of the *Proceedings of the 2nd International Symposium on Phosphorus Chemistry Directed Towards Biology*, Bruzik & Stec [Eds.], Lodz, Poland, Sep. 8–12, 1986, Elsevier Science Publishers, Amsterdam, The Netherlands, pp. 3–21.

Kierzek et al., (II), "Synthesis of 2'–5'–Oligoribonucleotides on Solid Support by Phosphoramidite Method, " *Biophosphates and Their Analogues–Synthesis, Structure, Metabolism and Activity*,report of the *Proceedings of the 2nd International Symposium on Phosphorus Chemistry Directed Towards Biology*, Bruzik & Stec [Eds.], Lodz, Poland, Sep. 8–12, 1986, Elsevier Science Publishers, Amsterdam, The Netherlands, pp. 179–184.

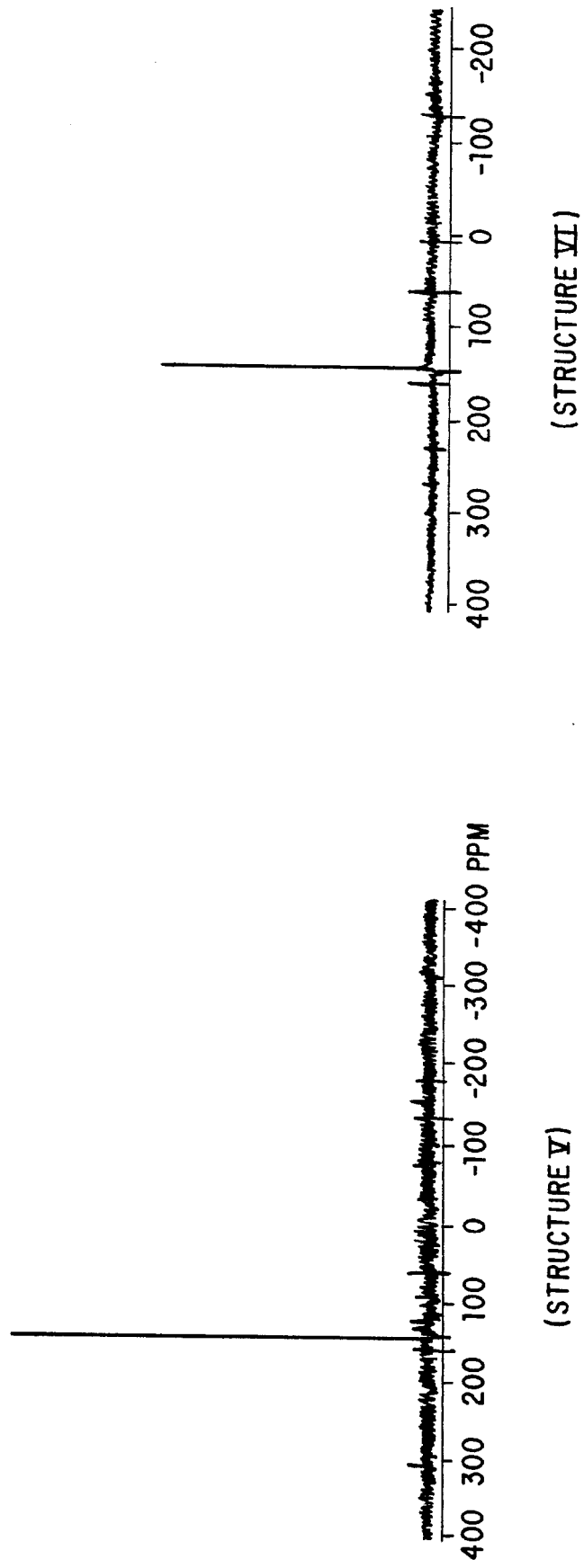

(STRUCTURE Xa)

(STRUCTURE XV)

(STRUCTURE XVIa)

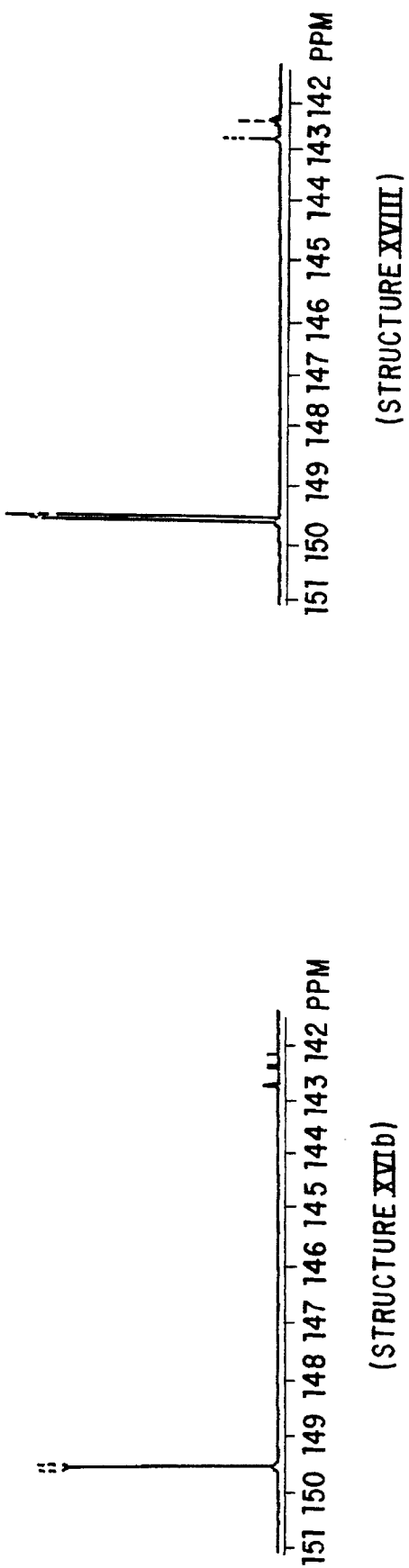

5,525,719

N-PROTECTED-2'-O-METHYL-AND N-PROTECTED-3'-O-METHYL-RIBONUCLEOSIDES AND THEIR PHOSPHORAMIDITE DERIVATIVES

CROSS-REFERENCE TO RELATED APPLICATION

This application is a continuation-in-part of U.S. application Ser. No. 07/753,077, filed Aug. 30, 1991, issued as U.S. Pat. No. 5,214,135 on May 25, 1993, which is herein incorporated by reference.

FIELD OF THE INVENTION

This invention relates to N-protected-2'-O-methyl- and N-protected-3'-O-methyl-ribonucleosides and their synthesis.

BACKGROUND OF THE INVENTION

One of the goals of molecular biology is to understand the biological information contained in DNA and RNA sequences. The use of synthetic, sequence defined DNA and RNA has played a key role in understanding the genetic code and various regulatory signals such as the operator, promoter, ribosomal binding sites, enhancers, and transposable elements. The synthetic approach not only provides a final proof of the roles of various DNA and RNA sequences but also offers an opportunity for further improvement in function for practical application. The application of synthetic genes, linkers, primers, and probes from both DNA and RNA has become a powerful tool in the cloning, sequencing, and isolation of genomic DNA.

The synthetic methodology for the synthesis of short oligoribonucleotides by the phosphodiester approach was developed in the 1960s by Khorana, H. G., *Pure Appl. Chem.* 17:349–381 (1968). Organic chemical syntheses of larger molecules of oligoribonucleotides have been attempted by using the phophodiester, phosphotriester, or phosphite triester methods. However, the discovery of RNA ligase has extended the possibilities for synthesizing RNA molecules such as tRNA. Before RNA can be synthesized, however, the starting monomers must be provided. In synthesizing sequence-defined RNA oligomers, the purity and correct structure of the monomer building blocks is critical.

Currently, reports are available on the synthesis of N-protected-2'-O-methyl-3'-O-chlorophenyl phosphotriester ribonucleosides (Inoue, H. et al., *FEBS Letters*, 215:327–330 (1987) "Inoue I") and N-protected-2'-O-methyl-3'-cyanoethyl phosphoramidite ribonucleosides (Sproat, B. S. et al., *Nucl. Acids Res.* 18:41–49 (1990)). The methyl iodide/silver oxide method developed by Inoue et al. (1987) on the seven membered bis-sililoxy protected (Markiewicz, W. T., *J. Chem. Res.* (S): 24–25 (1979)) uridine and $N^6$-cytidine generates the undesired 3'-O-methyl-isomers to the extent of 6–8%.

It is believed that methyl iodide in the Inoue method causes the partial ring opening, and subsequently leads to 3'-O-methyl-isomer formation. Similarly, the $CH_2N_2$ reaction under very mild reaction conditions still leads to formation of some 3'-O-methyl isomer (4–5%). This reaction is described in Inoue et al. (1987), as well as in Ekborg, G. et al., *J. Carbohyd. Nucleosides and Nucleotides*, 7:57–61 (1982) and Heikkila, J. et al., *J. Acta. Chem. Scand.*, B36:715–717 (1982).

It is therefore important to establish stringent purification techniques and a certain homogeneity of the phosphoramidites because of their use in RNA syntheses. In Sproat, B. S. et al., *Nucl. Acids Res.* 18:41–49 (1990)), discussing the synthesis of N-protected-2'-O-methyl-3'-cyanoethyl phosphoramidite ribonucleosides, the authors report only a single peak in $^{31}$P-NMR of $N^2$-(4-tertbutyl) benzamido-2'-O-methyl-3'-cyanoethyl phosphoramidite of guanosine.

Since these products are used directly in the synthesis of defined sequence RNA, the purity as well as absolute structure assignment is very critical for any biological application. Besides the concern for purity of these biochemicals, it is also advantageous to develop products which have the most commonly used protecting groups on the pyrimidine or purine ring system of these monomers. This is important for the convenience of the synthesizer and dramatically improves the quality of the 2'-O-methyl-RNA oligomers produced from these monomers. Thus, the $N^2$ isobutyryl group on guanosine and $N^6$ benzoyl on adenosine represent the most versatile protecting groups for the aforementioned purposes.

SUMMARY OF THE INVENTION

This invention is directed to processes for producing high purity N-protected-2'-O-methyl-5'-dimethoxytrityl-3'-ribonucleoside methoxy, N,N-diisopropyl phosphoramidites (group 1), and N-protected-2'-O-methyl-5'-dimethoxytrityl-3'-ribonucleoside ethoxy, N,N-diisopropyl phosphoramidites (group 2). This invention is further directed to the process for producing high purity 2'-O-methyl-5' dimethoxytrityl-inosine (structure IX; group 3), and 2'-O-methyl-5'-dimethoxytrityl-inosine-3'-cyanoethyl, N,N-diisopropyl phosphoramidite (structure X; group 3). This invention is also directed to the process for producing high purity N-protected-3'-O-methyl-5'-dimethoxytrityl ribonucleosides (group 6), and N-protected-3'-O-methyl-5'-dimethoxytrityl-2'-ribonucleoside cyanoethyl, N,N-diisopropyl phosporamidites (group 7).

The process involved in group 1 compounds produces the following (see TABLES 2 and 10):

$N^6$-benzoyl-2'-O-methyl-5'-dimethoxytrityl-adenosine-3'-methoxy-N,N-diisopropyl phosphoramidite (structure I);

$N^4$-benzoyl-2'-O-methyl-5'-dimethoxytrityl-cytidine-3'-methoxy-N,N-diisopropyl phosphoramidite (structure IIa);

$N^4$-isobutyryl-2'-O-methyl-5'-dimethoxytrityl-cytidine-3'-methoxy-N,N,-diisopropyl phosphoramidite (structure IIb);

$N^2$-isobutyryl-2'-O-methyl-5'-dimethoxytrityl-guanosine-3'-methoxy-N,N-diisopropyl phosphoramidite (structure III);

2'-O-methyl-5'-dimethoxytrityl-uridine-3'-methoxy-N,N-di-iso-propyl phosphoramidite (structure IVa); and 2'-O-methyl-5'-dimethoxytrityl-uridine-3'-cyanoethyl-N,N-diisopropyl phosphoramidite (structure IVb).

The process involved in group 2 produces the following compounds (see TABLES 3 and 10):

$N^6$-benzoyl-2'-O-methyl-5'-dimethoxytrityl-adenosine-3'-ethoxy-N,N-diisopropyl phosphoramidite (structure V);

$N^4$-benzoyl-2'-O-methyl-5'-dimethoxytrityl-cytidine-3'-ethoxy-N,N-diisopropyl phosphoramidite (structure VI);

$N^2$-isobutyryl-2'-O-methyl-5'-dimethoxytrityl-guanosine-3'-ethoxy-N,N-diisopropyl phosphoramidite (structure VII); and 2'-O-methyl-5'-dimethoxytrityl-uridine-3'-ethoxy-N,N-di-iso-propyl phosphoramidite (structure VIII).

The process involved in group 3 produces the following compounds (see TABLES 4, 5 and 10):

2'-O-methyl-5'-dimethoxytrityl-inosine (structure IX);

2'-O-methyl-5'-dimethoxytrityl-inosine-3'-cyanoethyl N,N-diisopropyl phosphoramidite (structure Xa);

2'-O-methyl-5'-dimethoxytrityl-inosine-3'-methoxy N,N-diisopropyl phosphoramidite (structure Xb); and 2'-O-methyl-5'-dimethoxytrityl-inosine-3'-ethoxy N,N-diisopropyl phosphoramidite (structure Xc).

The compounds of group 4 and group 5 are produced using the process disclosed for producing compounds of group II of parent patent application, Ser. No. 07/753,077.

The process involved for group 6 produces the following compounds (see TABLE 6):

$N^6$-benzoyl-3'-O-methyl-5'-dimethoxytrityl-adenosine (structure XI);

$N^4$-benzoyl-3'-O-methyl-5'-dimethoxytrityl-cytidine (structure XIIa);

$N^4$-isobutyryl-3'-O-methyl-5'-dimethoxytrityl-cytidine (structure XIIb);

$N^2$-isobutyryl-3'-O-methyl-5'-dimethoxytrityl-guanosine (structure XIII); and

3'-O-methyl-5'-dimethoxytrityl-uridine (structure XIV).

The process involved for group 7 produces the following compounds (see TABLES 8 and 10):

$N^6$-benzoyl-3'-O-methyl-5'-dimethoxytrityl-adenosine-2'-cyanoethyl N,N-diisopropyl phosphoramidite (structure XV);

$N^4$-benzoyl-3'-O-methyl-5'-dimethoxytrityl-cytidine-2'-cyanoethyl-N,N-diisopropyl phosphoramidite (structure XVIa);

$N^4$-isobutyryl-3'-O-methyl-5'-dimethoxytrityl-cytidine-2'-cyanoethyl-N,N-diisopropyl phosphoramidite (structure XVIb);

$N^2$-isobutyryl-3'-O-methyl-5'-dimethoxytrityl-guanosine-2'-cyanoethyl-N,N-diisopropyl phosphoramidite (structure XVII); and 3'-O-methyl-5'-dimethoxytrityl-uridine-2'-cyanoethyl-N,N-diisopropyl phosphoramidite (structure XVIII).

The process involved for group 8 produces the following compound (see TABLE 7):

$N^4$-isobutyryl-2'-O-methyl-5'-dimethoxytrityl-cytidine (structure XIX).

a. Structure I: $N^6$-bz-2'-O-methyl-5'-DMT-adenosine-3'-methoxy-N,N-diisoporpyl phosphoramidite;

b. Structure IIa: $N^4$-bz-2'-O-methyl-5'-DMT-cytidine-3'-methoxy-N,N-diisopropyl phosphoramidite;

c. Structure III: $N^2$-ibu-2'-O-methyl-5'-DMT-guanosine-3'-methoxy-N,N-diisopropyl phosphoramidite; and d. Structure IVa: 2'-O-methyl-5'-DMT-uridine-'-methoxy-N,N-diisopropyl phosphoramidite.

FIG. 2 shows the $^{31}$P-NMR spectra (300 MHz) of the 2'-O-methyl nucleoside 3'-ethoxy phosphoramidites in $CDCl_3$:

a. Structure V: $N^6$-bz-2'-O-methyl-5'-DMT-adenosine-3'-ethoxy-N,N-diisopropyl phosphoramidite;

b. Structure VI: $N^4$-bz-2'-O-methyl-5'-DMT-cytidine-3'-ethoxy,N,N-diisopropyl phosphoramidite;

c. Structure VII: $N^2$-ibu-2'-O-methyl-5'-DMT-guanosine-3'-ethoxy,N,N-diisoporpyl phosphoramidite; and d. Structure VIII: 2'-O-methyl-5'-DMT-uridine-'-ethoxy,N,N-diisopropyl phosphoramidite.

Figure 1B:
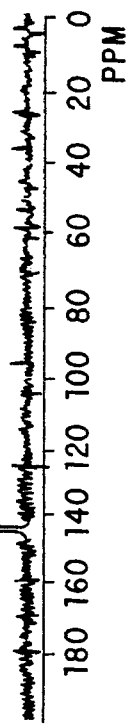
FIG. 1 shows the 31P-NMR spectra (300 MHz) of the 2'-O-methyl nucleoside 3'-methoxy phosphoramidites in $CDCl_3$.
Figure 1A:
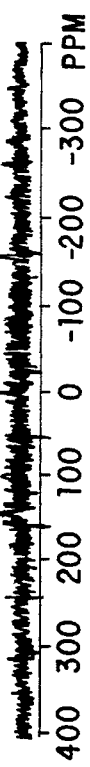
Figure 3:
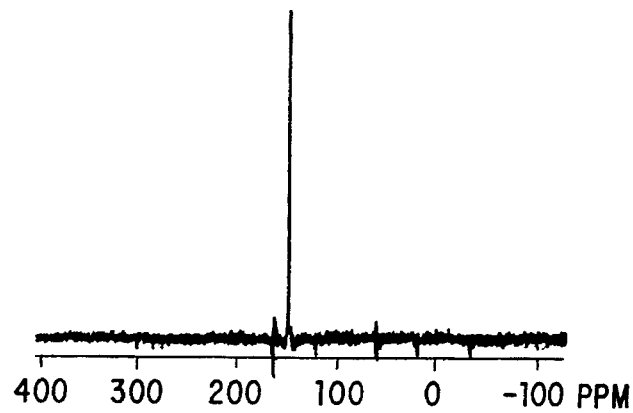

FIG. 3 shows the $^{31}$P-NMR spectra (300 MHz) of 2'-O-methyl-5'-DMT-inosine-3'-CNEt-N,N-diisopropyl phosphoramidite (Structure Xa).

Figure 4A:
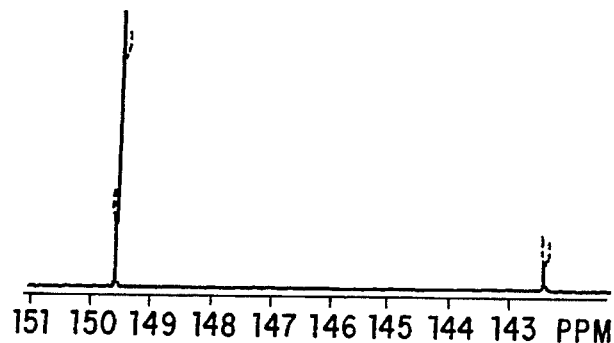
Figure 4B:
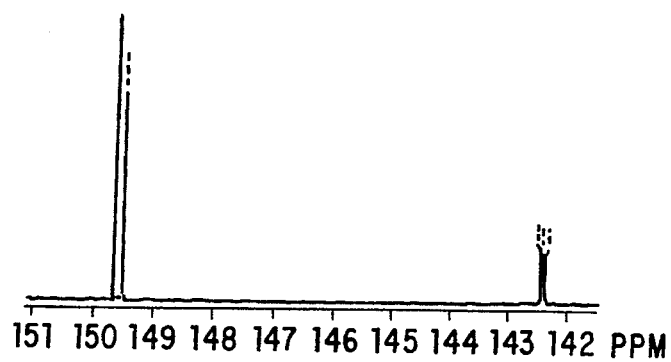

FIG. 4 shows the $^{31}$P-NMR spectra (300 MHz) of the 3'-O-methyl nucleoside 2'-cyanoethyl phosphoramidites:

a. Structure XV: $N^6$-bz-3'-O-methyl-5'-DMT-adensoine-2'-CNEt-N,N-diisopropyl phosphoramidite;

b. Structure XVIa: $N^4$-bz-3'-O-methyl-5'-DMT-cytidine-2'-CNEt-N,N-diisopropyl phosphoramidite;

c. Structure XVIb: $N^4$-ibu-3'-O-methyl-5'-DMT-cytidine-2'-CNEt-N,N-diisopropyl phosphoramidite; and d. Structure XVIII: 3'-O-methyl-5'-DMT-uridine-2'-CNEt-N,N-diisopropyl phosphoramidite.

DETAILED DESCRIPTION OF THE INVENTION

The reaction scheme for the synthesis of the compounds of this invention are depicted in the schematic representation. The symbols and abbreviations in the schematic follow standard nomenclature: A=Adenosine; G=Guanosine; C=Cytidine; and U=Uridine. The substituents at B or R are represented by standard symbols wherein N=nitrogen; Bz=Benzoyl; iBu=isobutyryl, FiMT represents monomethoxytrityl, DMT represents dimethoxytrityl, TMT represents trimethoxytrityl, isopropyl represents $NCH(CH_3)_2$. Where DMT is indicated, it will be understood that it can be substituted with either MMT or TMT.

"$N^6$-Protection of adenosine" is meant to include benzoyl, substituted benzoyl, other aroyls (such as naphthoyl), acetyl, substituted acetyl, phenoxyacetyl, and related compounds.

"$N^4$-Protection of cytidine" is meant to include benzoyl, substituted benzoyl, other aroyls (such as naphthoyl), acetyl, substituted acetyl, phenoxyacetyl, and related compounds.

"$N^2$-Protection of guanosine is meant to include isobutyryl, acetyl, substituted acetyls, phenoxyacetyl, and related compounds.

Preparation of 2'-O-Methyl-5'Dimethoxytrityl-Inosine (Structure IX)

5'-DMT-Inosine (10 mmole) was taken in DMF (250 ml), and $SnCl_2$ (0.3gm), and the solution was brought to −12° C. Diazomethane made according to the literature procedure (Robins, M. J., *J. Org. Chem.* 39:, 1891–1899 (1974), solution B, was added (105 ml) portionwise, during 4 hours, while maintaining the reaction temperature of −12° C., followed by stirring at 8°–10° C. for an additional 2 hours. Aqueous ammonia (5 ml) was added at 0° C., and then the solution was pumped out to remove DMF, followed by extraction with chloroform. The crude product was purified by column chromatography on silica gel (grade A), using chloroform and 1–10% methanol. The isolated yield of the pure desired product (structure IX) was 1.68 g (28%).

Procedure for the preparation of 2' and 3'-phosphoramidites purity greater than 99.54 (groups 1–2, and 7):

The appropriate precursor compounds have been described in parent application Ser. No. 07/753,077, herein incorporated by reference, and include: $N^6$-benzoyl-2'-O-methyl-5'-dimethoxytrityl adenosine; $N^4$-benzoyl-2'-O-methyl-5'-dimethoxytrityl cytidine; $N^2$-isobutyryl-2'-O-methyl-5'-dimethoxytrityl guanosine; and 2'-O-methyl-5'-dimethoxytrityl uridine. These are demonstrated with certain specific examples represented in group 1 and group 2. Further compounds, including those of group 3 (structure IX) and group 6 (represented by structures XI; XIIa; XIIb; XIII; XIV), were converted to corresponding phosphoramidites, group 3 (structures X) and group 7 (structures XV–XVIII), respectively, by modification of the procedure as described in Scaringe, S. A. et al., *Nucleic Acid Research* 18:5433-541 (1990).

Phosphitylation of the compounds (1 equivalent), with (N,N-diisopropyl amino) (cyanoethyl) phosphonamidic chloride, or (N,N-diisopropyl amino) (methyl) phosphonamidic chloride (structure XX), or (N,N-diisopropyl amino) (ethyl) phosphonamidic chloride (structure XXI) (2.5 equivalent), 2,4,6-collidine (3.5 equivalent), in freshly distilled peroxide free tetrahydrofuran (10 ml/mmole nucleoside), at 5° C., for 2.5 hours. The title compounds were purified by silicagel column chromatography (grade A). The gradient system was used based on the guidelines obtained with the RF values which were noted in the solvent systems listed in TABLE 1.

The pure fractions were monitored by thin layer chromatography and high pressure liquid chromatography (Rabbit-HP, Rainin Instruments Company), using a Rainin microsorb C-18 reverse phase column. The purest fractions obtained from the analytical data obtained above are then pooled together and dried. The products are then subjected to $^{31}$P-NMR analysis. This reveals phosphorus containing impurities which are generally present between 1–5%, between 0–100ppm. Isomeric impurities also show in the $^{31}$P-NMR analysis, generally a few ppm away from the desired peak. The isomeric impurities could range from 1–2%. The method of quantitation for the percent isomeric impurities have been discussed in parent patent application Ser. No. 07/753,077. The removal of the impurities at this stage is achieved by column chromatography in silica gel grade A, with the above gradient system, modifying the polarity as to reduce the rate of elution to approximately 10% less.

The final purity was established with $^{31}$P-NMR (TABLE 10), and the correct structural identity was determined by $^{1}$H NMR (TABLES 2–9).

It has been observed as a general rule that in $^{1}$H NMR, the methoxy groups on the aromatic rings (DMT-) and the 2'-O-methyl protons are much closer to each other, as compared to 3'-O-methyl protons. Conversely, the 3'-O-methyl protons are observed distinctly upfield, compared to 2'-O-methyl protons.

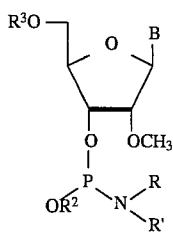

(GROUP 1)
Structures:
I; B; A$^{bz}$, R&R; Isopropyl, R$^{2}$; CH$_3$; R$^{3}$; DMT
II; B; C$^{bz}$; R&R; Isopropyl, R$^{2}$; CH$_3$; DMT
IIb; B; C$^{ibu}$; R&R; Isopropyl, R$^{2}$; CH$_2$CH$_2$CN; R$^{3}$; DMT
III; B; G$^{ibu}$; R&R; Isopropyl, R$^{2}$; CH$_3$; R$^{3}$; DMT
IVa; B; U; R&R; Isopropyl, R$^{2}$; CH$_3$; R$^{3}$; DMT
IVb; B; U; R&R; Isopropyl, R$^{2}$; CH$_2$CH$_2$CN; R$^{3}$; DMT

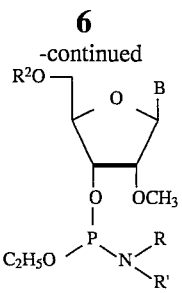

(GROUP 2)
Structures:
V; B; V; A$^{bz}$, R&R; Isopropyl; R$^{2}$; DMT
VI; B; C$^{bz}$, R&R; Isopropyl; R$^{2}$; DMT
VII; B; G$^{ibu}$, R&R; Isopropyl; R$^{2}$; DMT
VIII; B; U; R&R; Isopropyl; R$^{2}$; DMT

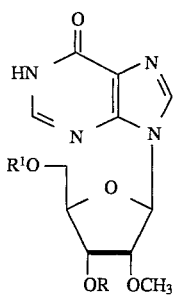

(GROUP 3)
Structure IX; R; H; R'; DMT
Structure Xa; R; P(OCH2CH2CN), N,N-Diisopropyl; R'; DMT
Structure Xb; R; P(OCH3), N,N-Diisopropyl; R'; DMT
Structure Xc; R; P(OC2H5), N,N-Diisopropyl; R'; DMT

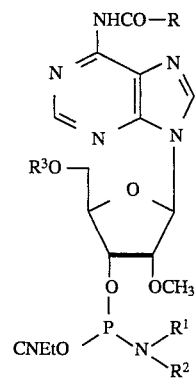

(GROUP 4)

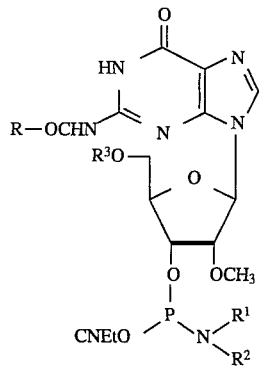

(GROUP 5)

-continued

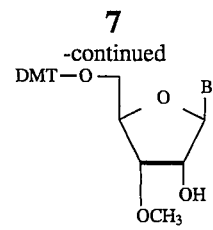

(GROUP 6)
Structure XI; B; $A^{bz}$
XIIa; B; $C^{bz}$
XIIb; B; $C^{ibu}$
XIII; B; $G^{ibu}$
XIV; B; U

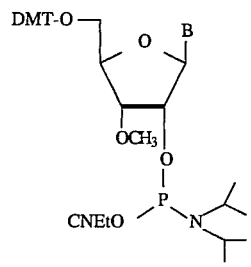

(GROUP 7)
Structure XV; B; $A^{bz}$
XVIa; B; $C^{bz}$
XVIb; B; $C^{ibu}$
XVII; B; $G^{ibu}$
XVIII; B; U

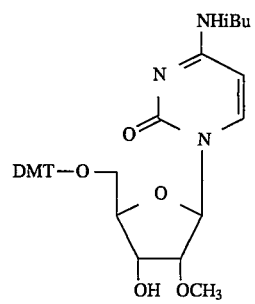

(GROUP 8)
Structure
(XIX)

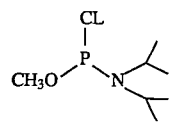

(XX)

-continued

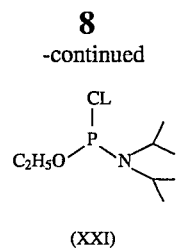

(XXI)

TABLE 1

$R_f$ VALUES
N-Protected-2'-O-Methyl/3'-O-Methyl-3'-hydrocarbyl/2'-hydrocarbyl ribonucleoside phosphoramidites

| Structure | Chromatographic Systems | | | | | | |
|---|---|---|---|---|---|---|---|
| | (a) | (b) | (c) | (d) | (e) | (f) | (g) |
| I | 0.61 | | | | | | |
| II | 0.61 | | | | | | |
| III | | 0.57 | | | | | |
| IV | 0.50 | | | | | | |
| V | | | 0.38 | | | | |
| VI | 0.46 | | | | | | |
| VII | | | | 0.50 | | | |
| VIII | 0.54 | | | | | | |
| IX | | | | | 0.28 | | |
| Xa | | | | | | 0.36 & 0.45 | |
| XI | | | | | | | 0.29 |
| XIIa | | | | | | | 0.15 |
| XIIb | | | | | | | 0.13 |
| XIV | | | | | | | 0.18 | chromatographic systems: (a), ethylacetate:hexane:triethylamine:: 50:40:10; (b), ethylacetate:methylenechloride:acetone:triethylamine:: 70:15:5:10; (c), ethylacetate:hexane:triethylamine:: 40:50:10; (d) ethylacetate:methylenechloride:acetone:triethylamine:: 60:20:10:10; (e) ethylacetate:chloroform:triethylamine:methanol:: 44:44:8:4; (f) ethylacetate:hexane:triethylamine:: 70:20:10, (g) chloroform:hexane:acetone:methanol:: 50:30:20:2

TABLE 2

$^1$H-NMR of N-Protected-2'-O-methyl-5'-dimethoxytrityl-nucleoside-3'-methoxy phosphoramidites (Structures I–IV)

| H-1' | H-2' | H-3' | H-4' | H-5'& H-5" | 2'-O CH3 | PO- CH3 | DMT- OCH3 | CH3 CH3 | CH— | Aromtics | | |
|---|---|---|---|---|---|---|---|---|---|---|---|---|
| N-6-Benzoyl-2'-O-methyl-5'-dimethoxytrityl-adenosine-3'-methoxy N,N-diisopropylphosphoramidite (structure I) | | | | | | | | | | | | |
| | | | | | | | | | | | H-2 | H-8 |
| 6.16– | 4.58 | 4.58 | 4.39 | 3.35 | 3.50 | 3.42 | 3.78 | 1.04 | 1.22 | 6.77 | 8.21 | 8.72 |
| 6.18& | — | — | — | — | 3.47& | — | — | — | — | — | & | & |
| 6.19– | 4.66 | 4.66 | 4.44 | 3.65 | 3.48 | | 1.18 | 1.28 | 8.03 | 8.24 | 8.73 | |

TABLE 2-continued

¹H-NMR of N-Protected-2'-O-methyl-5'-dimethoxytrityl-nucleoside-3'-methoxy phosphoramidites (Structures I–IV)

| H-1' | H-2' | H-3' | H-4' | H-5'& H-5" | 2'-O CH3 | PO- CH3 | DMT- OCH3 | CH3 \\ CH3 / | \\ CH— / | Aromtics | | |
|---|---|---|---|---|---|---|---|---|---|---|---|---|
| 6.21 td | | (2H) | | pi | ts | ths | | | | | | |

N-4-Benzoyl-2'-O-methyl-5'-dimethoxytrityl-cytidine-3'-methoxy N,N-diisopropylphosphoramidite (structure II)

| | | | | | | | | | | | H-5 | H-6 |
|---|---|---|---|---|---|---|---|---|---|---|---|---|
| 6.03 | 4.37 | 4.53 | 4.28 | 3.50 | 3.68 | 3.20 3.25; 3.37; 3.40 fs | 3.83 | 0.99 — 1.19 12H | 1.27 — 1.30 2H | 6.82 — 7.95 | 6.97 — 7.06 | 8.63 — 8.71 |
| 6.04 | 4.44 | 4.62 | 4.32 | 3.78 | — | | — | | | | | |

N-2-Isobutyryl-2'-O-methyl-5'-dimethoxytrityl-guanosine-3'-methoxy N,N-diisopropylphosphoramidite (structure III)

| | | | | | | | | | | | H-8 | (CH2)-Ring | CHCO |
|---|---|---|---|---|---|---|---|---|---|---|---|---|---|
| 5.81– 5.84& 5.89– 5.92 td | 4.59 — 4.66 | 4.75 — 4.84 | 4.26 — 4.32 | 3.49 — 3.60 | 3.47 & 3.43 ts | 3.42 & 3.77 ts | 3.76 & 3.77 | 0.98 — 1.18 12H | 1.19 — 1.30 2H | 6.72 — 7.64 | 7.80 — 7.82 | 0.67– 0.70& 0.86– 0.90 dq | 2.67 — 2.74 q |

2'-O-Methyl-5'-dimethoxytrityl-uridine-3'-methoxy,N,N-diisopropyl phosphoramidite (structure IV)

| | | | | | | | | | | | H-5 | H-6 |
|---|---|---|---|---|---|---|---|---|---|---|---|---|
| 5.97 — 6.01 td | 4.21– 4.53& 4.26– 4.65 | 4.43 & 5.55 | 3.80 — 3.85 | 3.48 & 3.66 | 3.58 & 3.59 | 3.55 3.56 | 3.80 — | 1.03 — 1.18 | 1.24 — 1.28 | 6.74 — 7.46 | 5.16 — 5.20 td | 8.04 — 8.13 td |

TABLE 3

¹H-NMR of N-Protected-2'-O-methyl-5'-dimethoxytrityl-nucleoside 3'-ethoxy phosphoramidites (Structures V–VIII)

| H-1' | H-2' | H-3' | H-4' | H-5'& H-5" | 2'-O CH3 | 3'-O CH2— | 3'-O C—CH3 | DMT- OCH3 | CH3 \\ CH3 | \\ CH— / | AROM TICS | | |
|---|---|---|---|---|---|---|---|---|---|---|---|---|---|

N-6-Benzoyl-2'-O-methyl-5'-dimethoxytrityl-adenosine-3-'-ethoxy, N,N-diisopropylphosphoramidite (structure V)

| | | | | | | | | | | | | H-2 | H-8 |
|---|---|---|---|---|---|---|---|---|---|---|---|---|---|
| 6.17 — 6.21 t | 4.59 — 4.68 m (2H) | 4.59 — 4.65 | 4.38 — 4.49 | 3.34 — 3.68 | 3.48 & 3.49 ts | 3.66 — 3.75 | 1.18 1.20 pi | 3.77 — | 1.06 1.21 p | 1.21 1.26 | 6.76 — 8.05 | 8.20 — 8.24 | 8.72– 8.73 |

N-4-Benzoyl-2'-O-methyl-5'-dimethoxytrityl-cytidine-3'-ethoxy, N,N-diisopropylphosphoramidite (structure VI)

| | | | | | | | | | | | | H-5 | H-6 |
|---|---|---|---|---|---|---|---|---|---|---|---|---|---|
| 6.04 — 6.06 | 4.35 — 4.44 | 4.53 — 4.63 | 4.28 — 4.34 | 3.46 — 3.74 | 3.68 & 3.69 | 3.65 3.90 pi | 1.19 1.26 pi | 3.827 & 3.831 | 1.00 1.20 | 1.29 1.37 | 6.83 — 7.91 | 6.96 — 7.04 | 8.63 — 8.73 |

N-2-Isobutyryl-2'-O-methyl-5'-dimethoxytrityl-guanosine-3'-ethoxy N,N-diisopropylphosphoramidite (structure VII)

| | | | | | | | | | | | | (H-8) | (CH3)2-Ring | CH—CO |
|---|---|---|---|---|---|---|---|---|---|---|---|---|---|---|
| 5.80– 5.82& 5.89– 5.92 td | 4.51 — 4.68 | 4.81 — 4.85 | 4.25 — 4.33 | 3.85 — 4.20 | 3.50 & 3.51 pi | 3.54 — 3.58 td | 1.23 1.31 | 3.76 — 3.77 | 0.84 — 1.15 | 1.40 — 1.59 | 6.72 — 7.65 | 7.77 — 7.83 | 0.62 — 0.74 | 3.03 — 3.13 |

2'-O-Methyl-5'-dimethoxytrityl-uridine-3'-ethoxy,N,N-diisopropyl phosphoramidite (structure VIII)

TABLE 3-continued

¹H-NMR of N-Protected-2'-O-methyl-5'-dimethoxytrityl-nucleoside 3'-ethoxy phosphoramidites (Structures V–VIII)

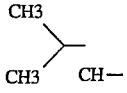

| H-1' | H-2' | H-3' | H-4' | H-5'& H-5" | 2'-O CH3 | 3'-O CH2— | 3'-O C—CH3 | DMT- OCH3 | CH3 | CH— | AROM TICS | | |
|---|---|---|---|---|---|---|---|---|---|---|---|---|---|
| | | | | | | | | | | | | H-5 | H-6 |
| 5.97 | 4.39 | 4.51 | 4.18 | NA | 3.53 & | 3.92 | 1.23 | 3.77 & | 0.95 | 1.29 | 6.78 | 5.12 | 8.03 |
| — | — | — | — | | | — | — | | — | — | — | — | — |
| 6.00 | 4.50 | 4.64 | 4.27 | | 3.54 | 4.13 | 1.28 | 3.79 | 1.20 | 1.37 | 7.47 | 5.22 Q | 8.14 Q |
| sd | tm | | | pi | td | | | td | | | | | |

TABLE 4

¹H-NMR of 2'-O-Methyl-5'-dimethoxytrityl-inosine (Structures IX)

| H-1' | H-2' | H-3' | H-4' | H-5'& H-5" | 2'-O CH3 | DMT- OCH3 | AROM TICS | H-2 | H-8 |
|---|---|---|---|---|---|---|---|---|---|
| 5.95 | 4.39 | 4.51 | 4.18 | NA | 3.56 | 3.75 | 6.75 | 7.93 | 7.85 |
| — | — | — | — | | | | | — | |
| 6.00 J=5.56 | 4.50 | 4.64 | 4.27 | | pi | 3.76 | 7.42 | 7.95 J=3.41 | |

TABLE 5

¹H-NMR of 2'-O-Methyl-5'-dimethoxytrityl-inosine- 3'-CNEt, N-N-diisopropylphosphoramidite (Structures Xa)

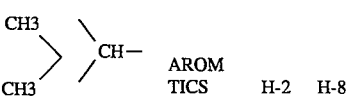

| H-1' | H-2' | H-3' | H-4' | H-5'& H-5" | 2'-O CH3 | OP- CH2 | CH2- CN | DMT- OCH3 | CH3 | CH— | AROM TICS | H-2 | H-8 |
|---|---|---|---|---|---|---|---|---|---|---|---|---|---|
| 6.09& 6.10 | 4.36 — | 4.79 — | 4.20 — | 3.23 — | 3.58 — | 3.50 — | 2.24& 2.42 | 3.78 | 0.92 — | 1.18 — | 6.78 — | 7.93 & | 7.87 & |
| — 6.13& 6.15 | 4.61 | 4.99 | 4.37 | 3.57 | 3.59 | 4.02 | — 2.53& 2.69 | | 1.16 | 1.30 | 7.45 | 8.02 | 7.88 |

TABLE 6

¹H-NMR of N-Protected-3'-O-Methyl-5'-dimethoxytrityl-nucleosides (Structures XI–XIV)

| H-1' | H-2' | H-3' | H-4' | H-5'& H-5" | 3'-O— CH3 | DMT- OCH3 | Aromtics | | |
|---|---|---|---|---|---|---|---|---|---|

N-6-Benzoyl-3'-O-Methyl-5'-dimethoxytrityl-adenosine (structure XI)

| | | | | | | | | H-2 | H-8 |
|---|---|---|---|---|---|---|---|---|---|
| 6.04 | 4.94 | 4.31 | 4.11 | 3.32– 3.38& | 3.45 | 3.77 | 6.78 | 8.20 | 8.73 |
| — | — | — | — | NA– 3.54 | | | — | — | — |
| 6.06 | 4.98 | 4.35 | 4.14 | | | | 8.06 | 8.23 | 8.74 |
| J=5.92 | | | | | | | | | |

N-4-Benzoyl-3'-O-methyl-5'-dimethoxytrityl-cytidine (structure XIIa)

| | | | | | | | | H-5 | H-6 |
|---|---|---|---|---|---|---|---|---|---|
| 5.79 | 4.31 | 4.27 | 4.24 | 3.33– 3.37& | 3.54 | 3.74 | 6.77 | 6.21 | 7.60 |
| — | — | — | — | 3.42– 3.47 | | | — | — | — |
| 5.80 | 4.33 | 4.30 | 4.25 | | | | 8.14 | 6.25 | 7.64 |
| J= | | | | | | | J=8.21 | J=7.64 | |

TABLE 6-continued $^1$H-NMR of N-Protected-3'-O-Methyl-5'-dimethoxytrityl-nucleosides
(Structures XI–XIV)

| H-1' | H-2' | H-3' | H-4' | H-5'& H-5" | 3'-O—CH3 | DMT-OCH3 | Aromtics | | | CH3 CH3 >CH | |
|------|------|------|------|------------|----------|----------|----------|---|---|---|---|
| 3.48 | | | | | | | | | | | |

N-4-Isobutyryl-3'-O-methyl-5'-dimethoxytrityl-cytidine (structure XIIb)

| 5.97 | 4.44 | 4.34 | 4.01 | 3.42–3.47& | 3.48 | 3.86 | 6.88 | 7.28 | 8.38 | 1.24 | 1.30 |
| — | — | — | — | | | | — | — | — | — | — |
| 5.98 | 4.46 | 4.36 | 4.05 | 3.58–3.62 | | | 7.44 | NA | 8.41 | 1.30 | 1.36 |
| J=2.13 | | | | | | | pi | J=7.61 | dd | q | |

3'-O-Methyl-5'-dimethoxytrityl-uridine (structure XIV)

| | | | | | | | | H-5 | H-6 | | |
|---|---|---|---|---|---|---|---|-----|-----|---|---|
| 5.90 | 4.29 | 4.15 | 3.94 | 3.37–3.38& | 3.40 | 3.78 | 6.80 | 5.37 | 7.74 | | |
| — | — | — | — | | | | — | — | — | | |
| 5.91 | 4.36 | 4.16 | 3.96 | 3.50–3.51 | | | 7.38 | 5.40 | 7.77 | | |
| J=4.57 | | | | | | | | J=8.21 | | | |

TABLE 7

$^1$H-NMR of N$^4$-Isobutyryl-2'-O-Methyl-5'-dimethoxytrityl-cytindine (Structure XIX)

| H-1' | H-2' | H-3' | H-4' | H-5'& H-5" | 2'-O CH3 | DMT-OCH3 | H-5 | H-6 | AROM TICS | CH3 CH3 >CH |
|------|------|------|------|------------|----------|----------|-----|-----|-----------|-------------|
| 5.99 | 3.98 | 4.36 | 3.76 | 3.48 | 3.73 | 3.80 | 7.04 | 8.49 | 6.82 | 1.18 NA |
| — | — | — | — | | | | — | — | — | — |
| 6.00 | 4.05 | 4.45 | 3.80 | 3.63 | | | 7.09 | 8.53 | 7.42 | 1.23 |
| J=NA | | | pi | dq | | | d | d | | pi |

TABLE 8

$^1$H-NMR of N-Protected-3'-O-Methyl-5'-dimethoxytrityl-nucleoside 2'-methoxy Phosphoramidites (Structures XV–XVIII)

| H-1' | H-2' | H-3' | H-4' | H-5'& H-5" | 3'-O CH3 | OP-CH2 | CH2-CN | DMT-OCH3 | CH3 CH3 >— | >CH | Aromtics | | |
|------|------|------|------|------------|----------|--------|--------|----------|-------------|-----|----------|---|---|

N-6-Benzoyl-3'-O-methyl-5'-dimethoxytrityl-adenosine-2'-CNEt N,N-diisopropylphosphoramidite (structure XV).

| | | | | | | | | | | | | H-2 | H-8 |
|---|---|---|---|---|---|---|---|---|---|---|---|------|------|
| 6.21 | 5.22 | 4.36 | 4.20 | 3.40–3.46& | 3.55 | 3.58 | 2.65 | 3.89 | 0.99–1.02& | 1.21 1.23& | 6.88 | 8.31 & | 8.77 & |
| — | — | — | — | | — | — | — | — | | — | — | | |
| 6.23 | 5.26 | 4.39 | 4.24 | 3.58–3.62 | | 3.62 | 2.71 | | 1.17–1.19 | 1.26 1.31 | 7.89 | 8.35 | 8.81 |

N-4-Benzoyl-3'-O-methyl-5'-dimethoxytrityl-cytidine-2'-CNEt N,N-diisopropylphosphoramidite (structure XVIa).

| | | | | | | | | | | | | H-5 | H-6 |
|---|---|---|---|---|---|---|---|---|---|---|---|------|------|
| 5.98 | 4.56 | 4.19 | 3.86 | 3.45 | 3.38–3.44– | 3.59 — | 2.56–2.66& 2.70– | 3.78 3.81 | 1.11 | 1.26 | 6.82 | NA | 7.56 |
| — | — | — | — | — | & | | | | — | — | — | — | — |
| 6.30 | 4.64 | 4.28 | 4.08 | 3.58 | 3.44–3.69 | | 2.82 | | 1.25 | 1.39 | 7.61 | pi | 7.64 t |
| m | m | m | m | m | | | | | | | | | |

N-2 Isobutyryl-3'-O-methyl-5'-dimethoxytrityl-guanosine-2'-CNEt N,N-diisopropylphosphoramidite (structure XVII).

TABLE 8-continued

1H-NMR of N-Protected-3'-O-Methyl-5'-dimethoxytrityl-nucleoside 2'-methoxy Phosphoramidites (Structures XV–XVIII)

| H-1' | H-2' | H-3' | H-4' | H-5'& H-5" | 3'-O CH3 | OP- CH2 | CH2- CN | DMT- OCH3 | $\mathrm{CH_3}{>}\mathrm{CH_3}$ | $>\mathrm{CH}/$ | Aromatics |
|---|---|---|---|---|---|---|---|---|---|---|---|
| | | | | | | | | | | | H-8 |
| 5.78 | 5.18 | 4.25 | 4.08 | 3.12– 3.16& | 3.49 & | 3.30 | NA | 3.81 | 0.72– 0.76&– | 1.16 | 6.82 7.80 & |
| 5.80 | 5.22 | 4.26 | 4.11 | 3.55– 3.59 | 3.51 | 3.35 | | 3.82 | 0.95– 1.0 | 1.22 | 7.60 7.84 |
| | | | | | ts | pi | | | | | |

3'-O-Methyl-5'-dimethoxytrityl-uridine-2'-CNEt,N,N-diisopropyl phosphoramidite (structure XVIII).

| | | | | | | | | | | | H-5 H-6 |
|---|---|---|---|---|---|---|---|---|---|---|---|
| 6.02 & | 4.52 | 4.19 | 4.02 | 3.72 — | 3.48 & | 3.51 | 2.66 | 3.85 | 1.21 | 1.29 | 6.88 5.33 8.07 |
| 6.10 | 4.58 | 4.28 | 4.10 | 4.02 pi | 3.54 ts | 3.72 pi | 2.75 tt | | 1.29 | 1.40 | 7.48 5.40 8.11 |

TABLE 9

1H-NMR of N4-Isobutyryl-2'-O-methyl-5'-dimethoxytrityl-cytidine-3'-CNEt, N,N-diisopropylphosphoramidite (Structure IIb)

| H-1' | H-2' | H-3' | H-4' | H-5'& H-5'" | 2'-O CH3 | P-O— CH2 | CH2— CN | DMT- OCH3 | $\mathrm{CH_3}$ $\mathrm{CH_3}$ | CH | AROM TICS |
|---|---|---|---|---|---|---|---|---|---|---|---|
| 5.99 | 4.51 | 4.30 | 4.21 | 3.40 | 3.63 | 3.68– | 2.52 | 3.79 | 1.13 | 1.28 | 6.78 |
| 6.01& | — | — | — | — | — | 3.78& | — | & | — | — | — |
| 6.03– | 4.61 | 4.40 | 4.29 | 3.60 | 3.64 | 4.03– | 2.63 | 4.00 | 1.28 | 1.38 | 7.43 |
| 6.05 | — | — | — | — | — | 4.25 | — | — | — | — | — |

| (CH3)2-RING | CH—C=O | H-5 | H-6 |
|---|---|---|---|
| 0.93– | 2.32 | 6.87– | 8.45– |
| 0.90& | — | 6.93& | 8.49& |
| 1.08– | 2.39 | 6.94– | 8.55– |
| 1.13 | — | 6.98 | 8.60 |

## = d = doublet; dd = doublet of doublets; dq = double quartet; fs = four singlets; m = multiplets; pi = present among interfering peaks; q = quartet; sd = sharp doublet; t = triple; t = td; two doublets; tm = two multiplets; ts = two singlets; tm = two multiplets; tt = two triplets; ths = three singlets.

RESULTS AND DISCUSSION

The general methods have been discussed in great details for the synthesis of 2'-and 3'-O-methyl-5'-DMT-N-protected nucleosides in the earlier patent application No. 07/753,077, filed Aug. 30, 1991. The purity criteria were established, and individual proton NMR peaks were assigned, to rigorously determine the correct structures.

Certain additional 2'-O-methyl-5'-dimethoxytritylnucleosides were added in the present investigation, as to increase the further usefulness of these products, as well as to demonstrate generality of the synthetic processes. This includes the compound N4-isobutyryl-2'-O-methyl-5'-dimethoxytrityl cytidine (structure XIX), and its subsequent conversion to the corresponding 3'-CNEt phosphoramidite (structure IIb). The structures of the 3'-O-methyl-5'-dimethoxytrityl-N-protected nucleosides have been established by 1H NMR and high resolution thin layer chromatography (group 6; Structures XI, XIIa, XIIb, XIII and XIV). These products have been purified to greater than 99.5% purity in the present investigation. After the filing of parent application Ser. No. 07/753,077, a report has appeared describing some of these compounds (E. Wagner et al., Nucleic Acids Research 19 (21): 5965–5971, (1991). However, the assignment of the structures in this article reveals significant differences in the NMR shifts of individual protons, as compared to the assignments presented here. Furthermore full proton assignments have not been made in the above mentioned article.

The 3'-O-methyl-5'-dimethoxytrityl-N-protected nucleosides (structures represented by group 6) have been converted to the corresponding 2'-CNEt phosphoramidites (group 7, structures, XV; XVI; XVIb; XVII; XVIII). The complete structural characterizations have been made by 1H-NMR, 31P-NMR and high resolution thin layer chromatography. Purification processes have resulted in the products with a purity in excess of 99.5% and greater.

Similarly, the characteristic structural features used to determine the compounds represented by group 4 (N6-protected-2'-O-methyl-5-dimethoxytrityl-adenosine cyanoethyl N, N-dialkyl-phosphoramidite), as well as the compounds represented by group 5 (N2-protected-2'-O-methyl-5'-dimethoxytrityl-guanosine cyanoethyl N, N-dialkyl phosphoramidite), have been presented in parent application Ser. No. 07/753,077, filed Aug. 30, 1991. These data include the complete $^1$H-NMR (300 MHz), $^{31}$P-NMR, and high resolution thin layer chromatography. These data in combination were able to confirm that the purity of certain of the compounds represented in group 4 and 5 in excess of 99.5% and higher.

Similarly, the compound 2'-O-methyl-5'-dimethoxytrityl uridine-3' CNEt N, N-diisopropyl phosphoramidite (structure IVb) was fully characterized in the parent patent application, using the same analytical techniques.

The compounds represented in group 1, specifically where $R^2$ represents $CH^3$, and the compounds in group 2, where phosphorus atom is attached with the ethoxy ($OC_2H_5$) group, extends the earlier investigation (application 07/753, 077) to novel 2'-O-methyl substituted phosphoramidites from the chemical point of view. Biologically, these compounds offer unique synthetic 2'-O-methyl RNA molecules, which will possess specific cell membrane permeability properties. The inherent antisense biological activities of the 2'-O-methyl RNA, and the associated better permeability properties would most likely make these precursors very useful products.

In summary, various ultrapure 2'-O-methyl and 3'-O-methyl-N-protected 5'-dimethoxytrityl nucleosides, and the corresponding 3'-and 2'- phosphoramidites have been prepared and fully characterized. The phosphoramidite contain cyanoethyl (CNEt), methoxy ($OCH_3$), ethoxy ($OC_2H_5$) groups on the phosphorus atoms. The CNEt containing phosphoramidites will produce 2'-O-methyl RNA with a natural phosphodiester bond, while methoxy ($OCH_3$), and ethoxy ($OC_2H_5$) containing phosphoramidites will produce 2'-O-methyl RNA with either partially or fully attached methoxy or ethoxy group at the internucleotide bonds. These RNAs will have a varying degree of cell membrane permeability properties.

Although the foregoing invention has been described in some detail by way of illustration and example for the purposes of clarity and understanding, it will be obvious to one skilled in the art that certain changes and modifications may be practiced within the scope of the appended claims.

What is claimed is:

1. An N-protected-2'-O-methyl-ribonucleoside with purity greater than 99.5% selected from the group consisting of:

$N^6$-protected-2'-O-methyl-5'-dimethoxytrityl adenosine-3'-methoxy N,N-dialkyl phosphoramidite;

$N^4$-protected-2'-O-methyl-5'-dimethoxytrityl cytidine-3'-methoxy N,N-dialkyl phosphoramidite;

$N^2$-protected-2'-O-methyl-5-dimethoxytrityl guanosine-3'-methoxy N,N-dialkyl phosphoramidite; and 2'-O-methyl-5'-dimethoxytrityl uridine-3'-methoxy N, N-dialkyl phosphoramidite.

2. An N-protected-2'-O-methyl-ribonucleoside with purity greater than 99.5% selected from the group consisting of:

$N^6$-protected-2'-O-methyl-5'-dimethoxytrityl adenosine-3'-ethoxy N,N-dialkyl phosphoramidite;

$N^4$-protected-2'-O-methyl-5'-dimethoxytrityl cytidine-3'-ethoxy N,N-dialkyl phosphoramidite;

$N^2$-protected-2'-O-methyl-5'-dimethoxytrityl guanosine-3'-ethoxy N,N-dialkyl phosphoramidite; and 2'-O-methyl-5'-dimethoxytrityl uridine-3'-ethoxy N, N-dialkyl phosphoramidite.

3. The compound $N^4$-isobutyryl-2'-O-methyl-5'-dimethoxytrityl cytidine.

4. An N-protected-3'-O-methyl-ribonucleoside selected from the group consisting of:

$N^6$-protected-3'-O-methyl-5'-dimethoxytrityl adenosine;

$N^4$-protected-3'-O-methyl-5'-dimethoxytrityl cytidine;

$N^2$-Protected-3'-O-methyl-5'-dimethoxytrityl guanosine; and

3'-0-methyl-5'-dimethoxytrityl uridine.

5. An N-protected-3'-O-methyl-ribonucleoside selected from the group consisting of:

$N^6$-protected-3'-O-methyl-5'-dimethoxytrityl adenosine-2'-cyanoethyl N,N-dialkyl phosphoramidite;

$N^4$-protected-3'-O-methyl-5'-dimethoxytrityl cytidine-2'-cyanoethyl N,N-dialkyl phosphoramidite;

$N^2$-protected-3'-O-methyl-5'-dimethoxytrityl guanosine-2'-cyanoethyl N,N-dialkyl phosphoramidite; and 3'-O-methyl-5'-dimethoxytrityl uridine-2'-cyanoethyl N, N-dialkyl phosphoramidite.

* * * * *